United States Patent
Ekerdt et al.

(10) Patent No.: US 11,202,844 B2
(45) Date of Patent: *Dec. 21, 2021

(54) SYSTEMS AND METHODS FOR SPRAYING OF SANITIZING OR DISINFECTING COMPOSITIONS WITH IMPROVED COMPATIBILITY

(71) Applicant: THE CLOROX COMPANY, Oakland, CA (US)

(72) Inventors: Barbara Ekerdt, Pleasanton, CA (US); William L. Smith, Pleasanton, CA (US); John Glauber, Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/841,945

(22) Filed: Apr. 7, 2020

(65) Prior Publication Data
US 2020/0230278 A1     Jul. 23, 2020

Related U.S. Application Data

(62) Division of application No. 15/986,687, filed on May 22, 2018, now Pat. No. 11,027,034.
(Continued)

(51) Int. Cl.
*A61L 2/22* (2006.01)
*B05B 9/04* (2006.01)
(Continued)

(52) U.S. Cl.
CPC ................... *A61L 2/22* (2013.01); *B05B 1/14* (2013.01); *B05B 9/042* (2013.01); *B05B 5/16* (2013.01)

(58) Field of Classification Search
CPC .. A61L 2/22; B05B 9/042; B05B 1/14; B05B 5/16
See application file for complete search history.

(56) References Cited

U.S. PATENT DOCUMENTS 8,366,023 B1    2/2013   Lin
2009/0148342 A1*  6/2009   Bromberg ................. A61L 2/23
                                                             422/37

FOREIGN PATENT DOCUMENTS

JP    2004130263 A    4/2004
WO   2011040424 A1    4/2011

OTHER PUBLICATIONS

Saint-Gobain Corp. (Year: 2013).*
(Continued)

*Primary Examiner* — Sean E Conley
*Assistant Examiner* — Brendan A Hensel
(74) *Attorney, Agent, or Firm* — Erin Collins

(57) ABSTRACT

This invention relates to systems, methods, and disinfecting compositions for spraying onto surfaces to be sanitized or disinfected. Methods may include providing an aqueous hypohalite disinfecting composition, and providing a spraying system that may include a hand-held spray nozzle through which the composition is sprayed during use, and a pump and associated tubing for conveying the composition to the hand-held spray nozzle. The tubing may be specifically selected to exhibit at least a 65% recovery (no more than 35% loss) of hypohalite after 24 hours of contact between the composition and the tubing. The method may further include conveying the composition from the reservoir to the spray nozzle, and spraying the composition through the nozzle, e.g., onto the target surface. A related system may include similar components. A dilute hypohalite disinfecting composition may be provided for use with the system and/or method. The system may allow interchangeable use of a quaternary amine disinfecting composition.

5 Claims, 4 Drawing Sheets

Related U.S. Application Data

(60) Provisional application No. 62/511,671, filed on May 26, 2017.

(51) Int. Cl.
 *B05B 1/14* (2006.01)
 *B05B 5/16* (2006.01)

(56) References Cited

OTHER PUBLICATIONS

Saint—Gobain Corporation, Tygon Application Specific Tubing, 2013, Internet URL: http://www.thecatalogroom.com/pdfstorage/Tygon-Tubing-Saint-Gobain-Performance-Plastics-Catalog-Free-e-Murdock.pdf; pp. 13, 22, 24-25.
PCT Search Report; PCT/US18/34210, dated Aug. 13, 2018.

\* cited by examiner

SYSTEMS AND METHODS FOR SPRAYING OF SANITIZING OR DISINFECTING COMPOSITIONS WITH IMPROVED COMPATIBILITY

CROSS-REFERENCE TO RELATED APPLICATIONS

The present application is a divisional of U.S. patent application Ser. No. 15/986,687, filed May 22, 2018, which claims the benefit of U.S. Provisional Patent Application No. 62/511,671, filed May 26, 2017. Each of the above-referenced applications is hereby incorporated by reference in its entirety.

BACKGROUND OF THE INVENTION

1. The Field of the Invention

The present invention relates to dispensing systems, associated methods, and dilute sanitizing or disinfecting compositions for spraying through such systems and methods. Such compositions may particularly include sanitizing and disinfecting compositions including a sanitizing or disinfecting active agent, such as a hypohalite.

2. Description of Related Art

Sophisticated spraying systems for spraying a liquid composition are available. For example, electrostatic induction charged spraying systems are available from ByoPlanet, as well as other suppliers. While such systems are available, the present inventors have discovered that there are incompatibility issues when attempting to spray a sanitizing or disinfecting bleach composition using such available spraying systems. Because of such issues, until now, it was not possible to achieve sanitization or disinfection efficacy of a given target surface using such available spraying systems. The present systems, methods and compositions address such issues.

BRIEF SUMMARY

The present invention relates to spraying systems, methods, and related dilute sanitizing or disinfecting compositions for dispensing through the spraying system. In one aspect, the present invention relates to a method for dispensing a dilute sanitizing or disinfecting composition (e.g., including a hypohalite sanitizing or disinfecting active agent) through a spraying system. Such a method may include providing an aqueous sanitizing or disinfecting composition, providing a spraying system including a reservoir for holding the aqueous composition, a hand-held spray nozzle through which the composition is sprayed during use, and a pump and associated tubing for conveying the bleach composition from the reservoir to the hand-held spray nozzle. The tubing may advantageously be specifically selected to exhibit at least a 65% recovery (i.e., no more than a 35% loss) of hypohalite after 24 hours of contact between the sanitizing or disinfecting composition and the associated tubing. The method further comprises conveying the composition from the reservoir to the hand-held spray nozzle and spraying the composition through the hand-held spray nozzle, onto a desired surface.

Another aspect of the present invention relates to a spraying system specifically configured for dispensing a dilute sanitizing or disinfecting composition in an efficacious manner (e.g., while reducing inactivation of the sanitizing or disinfecting active agent within the system, so as to provide a desired level of sanitization or disinfection to the surface being sprayed). The system may include a reservoir for holding the composition, a hand-held spray nozzle through which the aqueous composition is sprayed during use, and a pump and associated tubing for conveying the aqueous composition from the reservoir to the spray nozzle. Advantageously, the tubing may be specifically selected to have particular characteristics for ensuring compatibility with a hypohalite (e.g., sodium hypochlorite) sanitizing or disinfecting composition, as well as physical characteristics ensuring suitability for use with a peristaltic pump. For example, the tubing may exhibit at least a 65% recovery (i.e., no more than a 35% loss) of hypohalite after 24 hours of contact between the sanitizing or disinfecting composition and the tubing. The tubing may have a stiffness from 120 lb/in to 135 lb/in, and a compression force to closure (i.e., that force required to pinch the tubing closed) of from 20 $lb_f$ to 30 $lb_f$.

Another aspect of the present invention is directed to dilute hypohalite sanitizing or disinfecting compositions, e.g., such as may be used with and/or included within the presently described spraying systems. The composition itself may include water, and a hypohalite salt (e.g., sodium hypochlorite) at a relatively dilute concentration, such as 85 ppm to 200 ppm (e.g., more typically 150 ppm to 200 ppm). The sanitizing or disinfecting composition may have a pH not more than 11.5, or a pH of not more than 7 (e.g., less than 11.5, such as 7 to 11, or less than 7, such as 5.5 to 6.7), and the sanitizing or disinfecting composition may exhibit at least a 65% recovery (i.e., no more than a 35% loss) of hypohalite after 24 hours of contact between the composition and the tubing of the spraying system. The composition may further be configured to provide a hypohalite concentration of at least 85 ppm as sprayed onto a surface to be sanitized or disinfected, upon spraying through the spray nozzle of the spraying system. For example, some fraction of the hypohalite active agent may be lost due to contact with the tubing, and another fraction of the hypohalite active agent may be lost to volatilization upon exiting the spray nozzle. Thus, the hypohalite concentration of the composition as fed to the spraying system may be specifically tailored to ensure that a concentration of at least 85 ppm hypohalite is being delivered to the target surface being sanitized or disinfected.

The various components and parameters of the spraying system, method of use, and composition (e.g., tubing materials, composition pH, initial hypohalite concentration in the composition and the like) are thus carefully selected and controlled to ensure efficacious sanitization or disinfection of a target surface upon spraying the composition through the spraying system. In an embodiment, the spraying system may be an electrostatic spraying system, in which tiny droplets of the dilute sanitizing or disinfecting composition are electrostatically charged to greatly improve surface coverage of the target surface. Such electrostatic spraying ensuring that all surfaces, including the undersides of a given surface, are substantially uniformly coated with the dilute sanitizing or disinfecting composition.

Further features and advantages of the present invention will become apparent to those of ordinary skill in the art in view of the detailed description of preferred embodiments below.

BRIEF DESCRIPTION OF THE DRAWINGS

To further clarify the above and other advantages and features of the present invention, a more particular description of the invention will be rendered by reference to specific embodiments thereof which are illustrated in the drawings located in the specification. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Definitions

Figure 1:
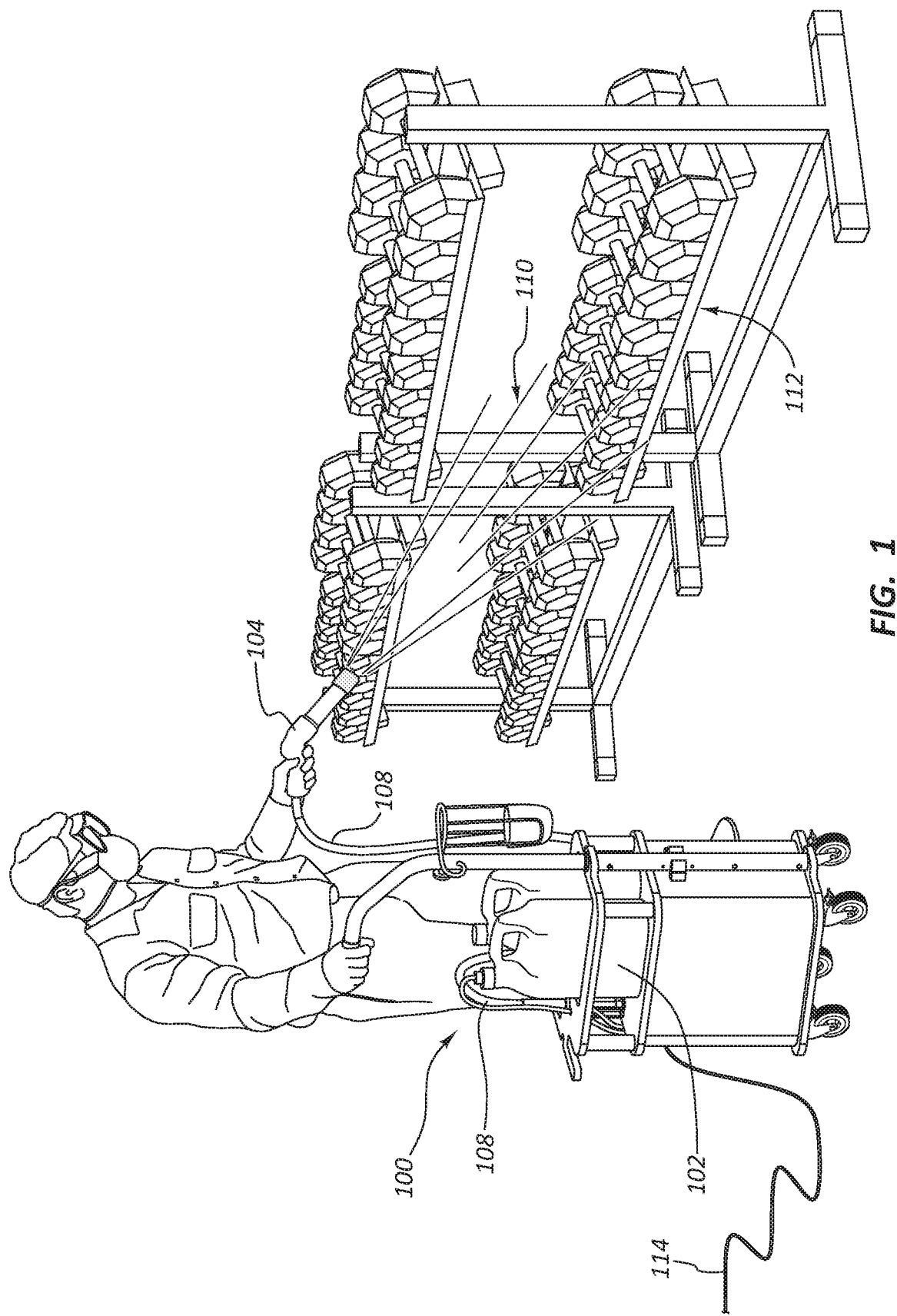
FIG. 1 is a perspective view showing use of an exemplary spraying system in an exemplary method of use.

Before describing the present invention in detail, it is to be understood that this invention is not limited to particularly exemplified systems or process parameters that may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

The term "comprising" which is synonymous with "including," "containing," or "characterized by," is inclusive or open-ended and does not exclude additional, unrecited elements or method steps.

The term "consisting essentially of" limits the scope of a claim to the specified materials or steps "and those that do not materially affect the basic and novel characteristic(s)" of the claimed invention.

The term "consisting of" as used herein, excludes any element, step, or ingredient not specified in the claim.

It must be noted that, as used in this specification and the appended claims, the singular forms "a," "an" and "the" include plural referents unless the content clearly dictates otherwise. Thus, for example, reference to a "surfactant" includes one, two or more surfactants.

The compositions described herein may provide sanitization, disinfection, or sterilization. As used herein, the term "sanitize" shall mean the reduction of contaminants in the inanimate environment to levels considered safe according to public health ordinance, or that reduces the bacterial population by significant numbers where public health requirements have not been established. By way of example, an at least 99% reduction in bacterial population within a 24 hour time period is deemed "significant." Greater levels of reduction are possible, as are faster treatment times (e.g., within 1 minute), when sanitizing. As used herein, the term "disinfect" shall mean the elimination of many or all pathogenic microorganisms on surfaces with the exception of bacterial endospores. As used herein, the term "sterilize" shall mean the complete elimination or destruction of all forms of microbial life and which is authorized under the applicable regulatory laws to make legal claims as a "sterilant" or to have sterilizing properties or qualities. Some embodiments of the present compositions provide for at least a 2 or more log reduction in bacterial population within a designated time period (e.g., 1 minute, 3 minutes, or the like). A 2-log reduction is equivalent to a 99% reduction, a 3-log reduction is equivalent to at least a 99.9% reduction, a 4-log reduction is equivalent to at least a 99.99% reduction, a 5-log reduction is equivalent to at least a 99.999% reduction, etc.

Unless otherwise stated, all percentages, ratios, parts, and amounts used and described herein are by weight.

Numbers, percentages, ratios, or other values stated herein may include that value, and also other values that are about or approximately the stated value, as would be appreciated by one of ordinary skill in the art. As such, all values herein are understood to be modified by the term "about". A stated value should therefore be interpreted broadly enough to encompass values that are at least close enough to the stated value to perform a desired function or achieve a desired result, and/or values that round to the stated value. The stated values include at least the variation to be expected in a typical manufacturing or formulation process, and may include values that are within 10%, within 5%, within 1%, etc. of a stated value. Furthermore, where used, the terms "substantially", "similarly", "about" or "approximately" represent an amount or state close to the stated amount or state that still performs a desired function or achieves a desired result. For example, the term "substantially" "about" or "approximately" may refer to an amount that is within 10% of, within 5% of, or within 1% of, a stated amount or value.

Some ranges may be disclosed herein. Additional ranges may be defined between any values disclosed herein as being exemplary of a particular parameter. All such ranges are contemplated and within the scope of the present disclosure.

In the application, effective amounts are generally those amounts listed as the ranges or levels of ingredients in the descriptions, which follow hereto. Unless otherwise stated, amounts listed in percentage ("%'s") are in weight percent (based on 100% active) of the composition.

The phrase 'free of' or similar phrases if used herein means that the composition comprises 0% of the stated component, that is, the component has not been intentionally added to the composition. However, it will be appreciated that such components may incidentally form, under some circumstances, as a byproduct or a reaction product from the other components of the composition, or such component may be incidentally present within an included component, e.g., as an incidental contaminant.

The phrase 'substantially free of' or similar phrases as used herein means that the composition preferably comprises 0% of the stated component, although it will be appreciated that very small concentrations may possibly be present, e.g., through incidental formation, as a byproduct or a reaction product from the other components of the composition, incidental contamination, or even by intentional addition. Such components may be present, if at all, in amounts of less than 1%, less than 0.5%, less than 0.25%, less than 0.1%, less than 0.05%, less than 0.01%, less than 0.005%, or less than 0.001%. In some embodiments, the compositions may be free or substantially free from any components not mentioned within this specification.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

II. Introduction

In an aspect, the present invention is directed to methods and systems for dispensing a dilute sanitizing or disinfecting composition through a spraying system. Such a method may include providing an aqueous sanitizing or disinfecting (e.g., including a hypohalite active agent) composition, providing a spraying system, conveying the composition through the spraying system to a hand-held spray nozzle of the spraying system, and spraying the composition onto a target surface to be disinfected, sanitized, or even sterilized. The term "disinfect" may principally be used in the present detailed description for brevity, although it will be appreciated that the systems, methods and compositions described herein may provide sanitization, disinfection, and/or sterilization.

The spraying system may include a reservoir for holding the bleach composition, a hand-held spray nozzle through which the aqueous disinfecting composition may be sprayed during use, a pump (e.g., a peristaltic pump) and associated tubing for conveying the disinfecting composition from the reservoir to the hand-held spray nozzle. The tubing may be particularly selected to exhibit at least a 65% recovery of hypohalite after 24 hours of contact between a disinfecting composition including hypohalite and the associated tubing. Such selection ensures that the tubing does not decrease efficacy of the disinfecting composition to an unacceptable degree, which might interfere with the ability to successfully achieve the desired disinfection.

The present spraying systems, methods and associated compositions advantageously provide the ability to deliver a disinfecting composition including an disinfection active agent, such as a hypochlorite salt, another hypohalite, hypochlorous acid, or the like), even where such agent may typically present incompatibility issues with typical tubing or other typical spraying system components which the composition including the active agent comes in contact with. For example, as described above, the inventors have found that typical materials employed in existing spraying systems exhibit an unacceptably high incompatibility level (e.g., very low recovery of hypohalite active agent) after contact between existing disinfecting compositions and such tubing or other components. The result is that if one were to use such existing systems with existing disinfecting bleach compositions, the desired disinfection cannot reliably be provided, as too much of the hypochlorite or other active agent is being inactivated before being sprayed onto the desired target surface to be disinfected. Furthermore, volatilization of such active agent upon exiting the spray nozzle should also be accounted for, as such volatilized active agent is unavailable for deposition on the target surface being disinfected.

The present systems, methods, and compositions provide specific selections for such components as the tubing of the spraying system, the pH and hypohalite concentration of the bleach composition, and other factors to ensure that the desired disinfection does in fact reliably occur.

III. Exemplary Spraying Systems, Methods, and Compositions

Figure 2:
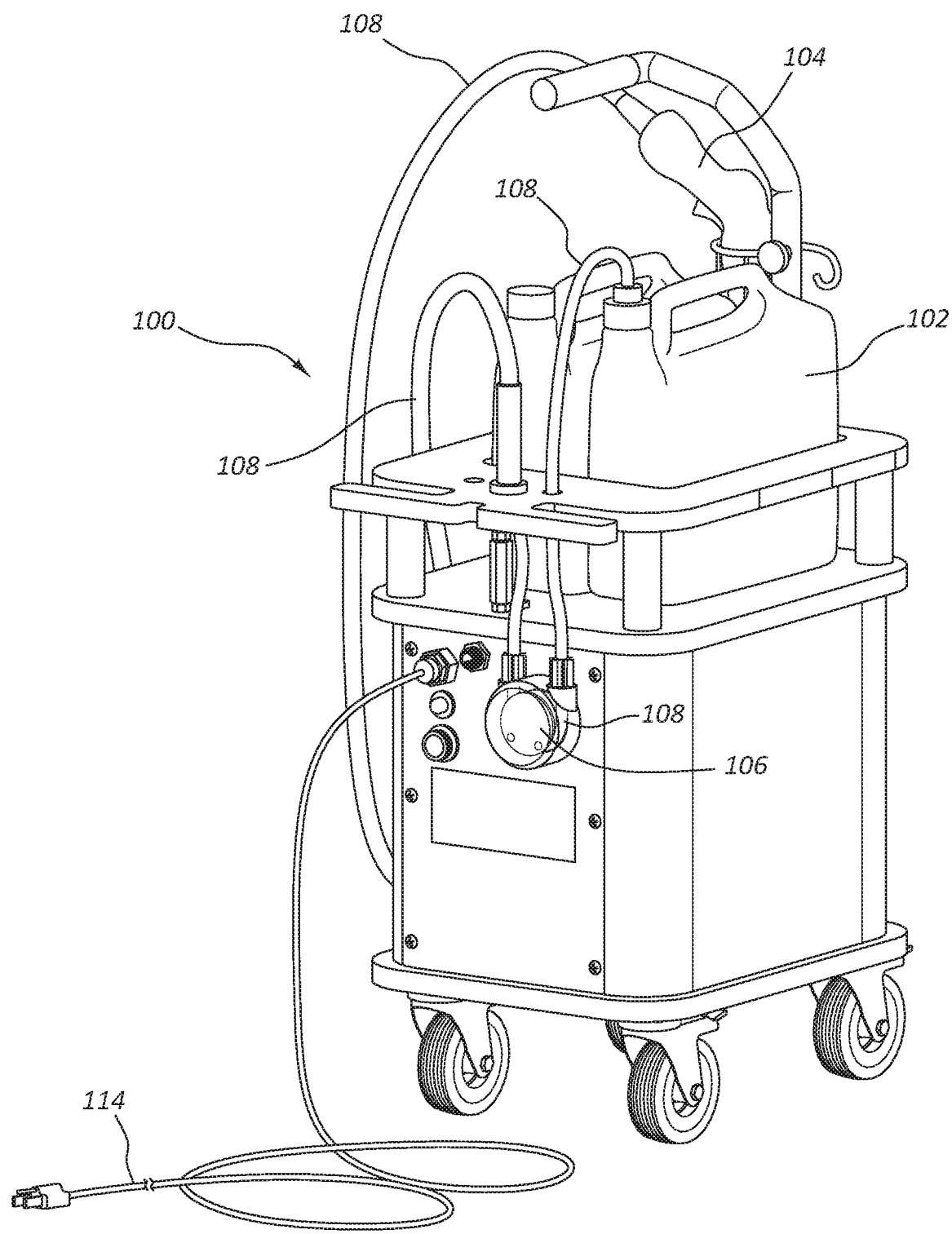
FIG. 2 is a perspective view of the system and method of FIG. 1, from another perspective.

FIGS. 1-2 illustrate an exemplary spraying system 100, as well as show an associated method of use. System 100 is shown as including a reservoir 102, which may be as simple as a jug or other container 102 for holding the aqueous disinfecting composition 110. For example, the system does not necessarily need to include any dedicated reservoir into which the composition 110 is poured, but rather the composition 110 may simply be provided through tubing 108, which delivers the disinfecting composition 110 from container 102 to the remainder of the system 100 (e.g., through pump 106, eventually to hand-held spray nozzle 104). Of course, other embodiments of a spraying system could include a dedicated reservoir separate from a jug or other container in which the disinfecting composition is provided by a supplier (e.g., such as CLOROX). In such alternative configurations, the disinfecting composition could be poured by the user into a dedicated reusable reservoir.

System 100 includes a hand-held spray nozzle 104 through which the disinfecting composition 110 is sprayed during use. In an embodiment, the hand-held spray nozzle 104 may be configured for electrostatic spraying, e.g., where the composition 110 being sprayed is electrostatically charged upon exiting nozzle 104 to improve coverage of the target surface 112 being sprayed. Examples of such electrostatic spraying systems are described in U.S. Pat. Nos. 5,704,554; 5,765,761; 9,138,760; and 9,144,811. Such spraying systems are available from BYOPLANET, located in Sunrise, Fla. Of course, any other spraying system could alternatively be used, whether an electrostatic spraying system or otherwise. Electrostatic spraying systems may be preferred because of the improved coverage and efficacy associated with such systems.

FIGS. 1-2 illustrate how spraying system 100 may be configured as a portable wheeled cart, including a power source (e.g., such as power cord 114) for providing power for powering pump 106, as well as providing power for induction charging to achieve electrostatic spraying of the composition through hand-held nozzle 104. Such configuration is merely exemplary, as a wide variety of spraying systems may suitably incorporate the principles described herein.

FIG. 2 shows system 100 including a pump 106 and associated tubing 108 for conveying the bleach composition 110 from container 102 to hand-held spray nozzle 104. At least a portion, and preferably all such tubing 108 exhibits at least a 65% recovery (i.e., no more than a 35% loss) of hypohalite after 24 hours of contact between the disinfecting composition and the tubing 108 (e.g., as measured at 70° F.). By way of example, the tubing may be specifically selected to exhibit at least a 65% recovery, at least a 70% recovery, at least a 75% recovery, or higher recovery. In other words, the tubing may be selected to exhibit no more than a 35% loss, no more than a 30% loss, or no more than a 25% loss, after 24 hours of contact between the tubing 108 and the disinfecting composition 110.

For example, the present inventors found that typical tubing materials employed in existing spraying systems exhibit lower, unacceptable recovery values, such as less than 60% recovery (i.e., more than a 40% loss) of hypochlorite or other hypohalite. The tubing materials according to the present invention are therefore specifically selected to ensure higher recovery (i.e., lower loss) of the hypochlorite or other hypohalite active agent in the disinfecting composition. For example, the present inventors have found that plasticizers and/or other adjuvants included in tubing materials typical employed in spraying systems are incompatible with the hypochlorite or other active agent(s), leading to the unacceptable levels of disinfecting active agent loss.

The selected tubing should thus meet various particular parameters in order to be suitable for use within the present spraying systems and methods. In addition to the above described need for minimal or at least reduced inactivation of the hypochlorite disinfecting active component, the tubing in at least some embodiments should be transparent or translucent, rather than opaque. Such a characteristic advantageously allows the user to view the composition passing through the tubing, on its way to the hand-held spray nozzle. Such ability to view the flow of composition through the tubing aids the user in ensuring that proper flow (e.g., no clogging, etc.) is occurring.

In addition, the selected tubing may be required to meet particular characteristics relative to its flexibility and durability, particularly where the pump employed in the spraying system is a peristaltic pump, such as peristaltic pump 106 shown in FIG. 2. Peristaltic pumps will be familiar to those of skill in the art, and typically include a rotor with one or more rollers (also referred to as "shoes) attached to the rotor, which rollers compress the flexible tube which passes around the rotor of the peristaltic pump, along a relatively tight radius of curvature (e.g., no more than about 6 inches, no more than about 5 inches, no more than about 4 inches, no more than about 3 inches. For example, as shown in FIG. 2, a peristaltic pump 106 that requires the tube to bend around a 6 inch circle would require the tubing to bend with a radius of curvature of 3 inches. As the rotor turns, the roller compresses the tubing 108, pinching it closed and forcing the fluid therein to move through the tubing 108.

Within spraying systems including a peristaltic pump according to the present invention, the inventors have found that it is advantageous that the tubing 108 contacted by the rollers of the peristaltic pump 106 have a stiffness that is from 120 $lb_f$/in to 135 $lb_f$/in. Somewhat related to tube stiffness, the selected tubing 108 may exhibit a compression force to closure that is from 20 $lb_f$ to 30 $lb_f$. Such compression force to closure refers to the force needed to cause the orifice within the tubing 108 to close (i.e., the pinching force required to close the orifice of the tube). Where the tubing material is too stiff and/or exhibits too high of compression force to closure, the rollers of a peristaltic pump 106 may not be able to effectively compress the tubing and pinch it closed to achieve the desired fluid flow. Where the tubing material has very low stiffness and/or compression force to closure is too low, pressure build up may occur within the tubing, causing the fluid in the tube to continue to spurt even after the user has finished spraying. In addition, tubing with very low stiffness and/or very low compression force to closure may not exhibit sufficient robustness or durability for use with a peristaltic pump. For example, ripping and/or shredding of the tubing material may occur after only a relatively short period of operation where the tubing material is not sufficiently stiff.

There is thus something of a delicate balance required to ensure that the tubing material is sufficiently stiff to ensure robustness and durability so as to provide long service life when used with a peristaltic pump, but not so stiff as to be incapable of accepting the needed tight radius of curvature as the tubing wraps around the peristaltic pump. The tubing 108 cannot be so stiff as to be too difficult to compress, forcing the orifice to close, as this will make use with a peristaltic pump impractical if not impossible, and the tubing 108 cannot exhibit a very low force to closure, which has been found to be associated with undesirable spurting of the composition even after use of the spray nozzle has stopped, because of a build up of pressure within the tubing 108. Finally, the tubing needs to exhibit low loss of hypohalite active agent upon contact with the disinfecting composition. As such, it is important to select the particular tubing material with care, to ensure that it meets the lengthy list of important criteria. Tubing materials currently employed in peristaltic pump spraying system applications do not meet such criteria.

In addition to the above criteria for tubing 108, the tubing may have a durometer value of 60 to 75, on the Shore A scale. While durometer can be helpful in identifying a suitable tubing material, durometer value only captures the response of the tubing material to indentation of the tubing wall, which characteristic appears to be insufficient to fully identify a material exhibiting acceptable stiffness and flexibility characteristics, as will be apparent from the exemplary tested materials, described in conjunction with Table 1, below. For example, VITON tubing has a durometer value of 60 to 75 on the shore A scale, but in testing, this tubing material was found to have too low of stiffness (less than 60 $lb_f$/in) and compression force to closure that was also too low (13.3 lbf). Before the importance of the stiffness and compression force to closure criteria were recognized by the present inventors, VITON was identified as a prospective suitable tubing material, based on its durometer value. When tested for use in a peristaltic pump, however this tubing material caused the composition to spurt even after spraying was finished, and the tubing material ripped up within 72 hours of usage under test conditions when used with a peristaltic pump. While the durometer value appeared to be acceptable, the stiffness and force to closure values (unrecognized at the time) were unacceptable. The inventors' experience with the VITON tubing material helped in identification of the above described criteria relating to stiffness and compression force to closure.

Other physical characteristics may also be of some utility for identifying suitable tubing materials. For example, tensile strength is the maximum stress a material can withstand while stretching or pulling, before breaking. Ultimate elongation is the maximum length a material can be stretched before breaking. Compression is another possible characteristic. Compression set for tubing materials describes to what extent the tubing will recover to its original shape after being compressed for an extended period of time under a heated condition. According to one test, a sample is compressed 25% at 70° C. for 22 hours to determine compression set (i.e., percentage of the original deflection retained after the material is allowed to recover at standard conditions (e.g., 20° C.) for 30 minutes. While such characteristics may be helpful to some extent, the present inventors have found that stiffness values, compression force to closure, and hypochlorite loss are far more useful in identifying potential suitable tubing materials.

As described above, the stiffness of suitable tubing materials, particularly for use with a peristaltic pump, may be from 120 $lb_f$/in to 135 $lb_f$/in. Stiffness measures the amount that a material resists deformation from an applied force. Stiffness can be measured by applying a force in one direction and measuring the rate of force per length of displacement. In compressing tubing at a constant rate of motion (e.g., as in a typical peristaltic pump), the rate of force per unit distance will give stiffness of the tubing material in the sidewall. Test results for such testing are shown in FIG. 3. The slope of the initial rise of the various curves shown in FIG. 3 thus corresponds to the stiffness of the various tested tubing materials. The force at which the rate significantly increases (i.e., the inflection point) corresponds to the compression force required to complete orifice closure. After this point, the compressive force is merely compressing the plastic tubing.

Figure 3:
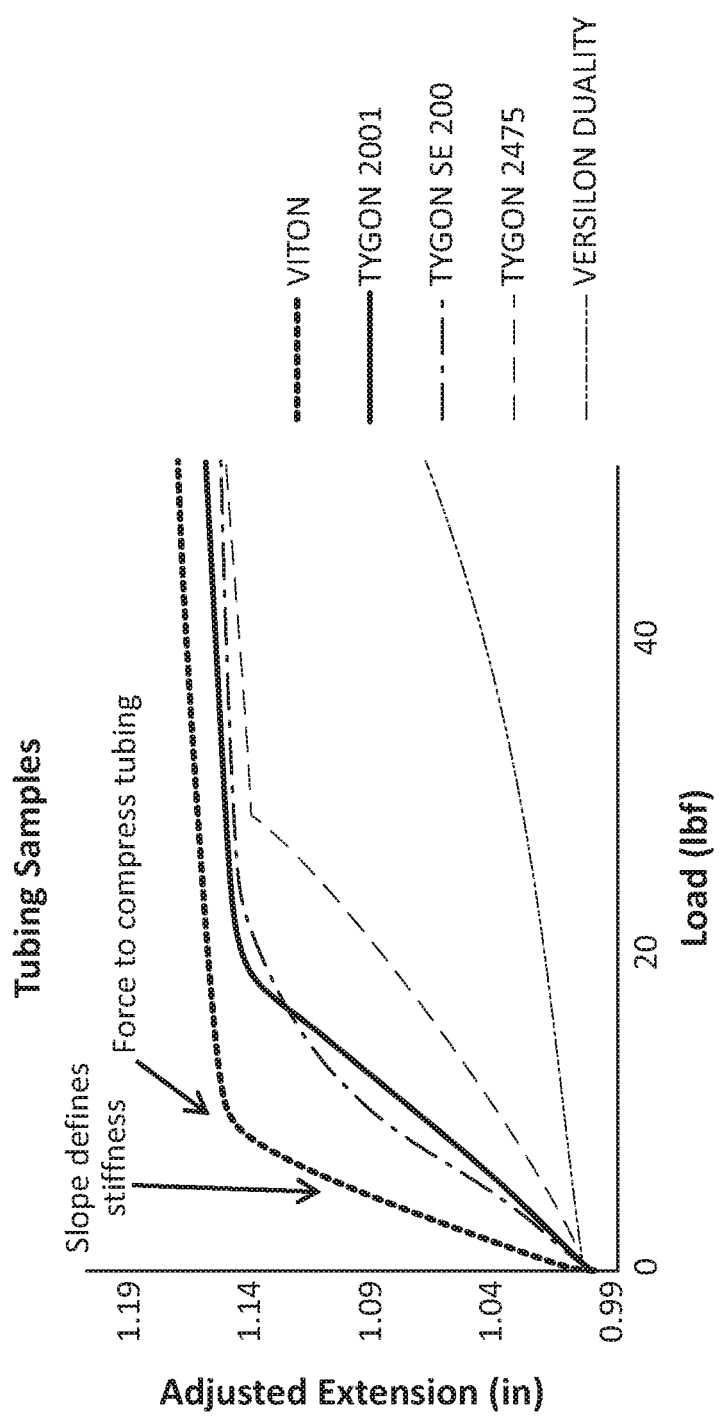
FIG. 3 shows stiffness and force to orifice closure characteristics as measured for various tubing materials.

The stiffness and compression force to closure shown in FIG. 3 and in Table 1 were determined by placing tubing samples flat along the bottom plate of an INSTRON testing machine. The INSTRON top plate (3"×0.5") was placed immediately above the tubing, perpendicular to the direction of the tubing. The top plate was lowered at a rate of 1 inch/minute until a maximum load of 300 $lb_f$ was reached, and then the plate was lifted again. The slope (in $lb_f$/in) (corresponding to the stiffness of the tubing material) was determined by compressing the top wall of the tube into eventual contact with the lower tube wall. The load at which the slope changed due to compression of the abutting tube walls signals the point of orifice closure. The tubing dimensions for all but the PVC material were 1/8" ID, 1/4" OD. The PVC tubing material that was tested was 3/16" ID, 5/16" OD. It will be appreciated that any size tubing could be used.

As described above, a peristaltic pump typically operates by alternatingly compressing and relaxing the tubing in a circular pump casing (e.g., see pump 106 of FIG. 2) to draw the contents of the tubing 108 through the tube. Generally such pumps include two rollers (sometimes referred to as shoes) which rotate at the same rate. Once a roller touches the tubing 108, it compresses the tubing completely (closing the orifice). As it rotates, it pushes the fluid through the tubing. Because of the physical demands imposed by such a pump system, it is important that the tubing material be elastomeric. Furthermore, where the composition is a disinfecting composition including a hypochlorite or other disinfecting active agent, the tubing needs to be chemically resistant to the composition being delivered therethrough, as described herein.

Existing spraying systems typically include multiple tubing sections, what at least two different materials are used for the various tubing sections. Such construction is typical to provide tubing that is appropriate to the flexibility and other needed characteristics for the given tubing section. For example, EXCELON RNT tubing material is currently used within existing spraying systems for the tubing section associated with the peristaltic pump, due to desirable flexibility, stiffness, and durability characteristics. The present inventors found that such tubing undesirably interacts with the hypohalite active agent in the disinfecting composition, due to the presence of plasticizers in the tubing material.

As a first iteration, the present inventors tested EXCELON RNT tubing in the peristaltic pump section, and low density polyethylene (LDPE) for the rest of the liquid tubing sections, because polyethylene has good chemical resistance, and would be less likely to interact with the bleach active agent. This was found to be impractical, because LDPE is relatively inflexible, making it difficult to work with, even in the tubing sections separate from the peristaltic pump. As a result of the difficulties of this first iteration, various other tubing materials were evaluated for stiffness versus flexibility, force to orifice closure, compatibility with hypochlorite active agents, and other characteristics. The results are shown in Table 1.

TABLE 1

| Tubing | % OCl⁻ Recovered | Stiffness (lbf/in) | Compression Force to Closure (lbf) | Durometer | Tensile Strength (psi) | Clear/Opaque |
|---|---|---|---|---|---|---|
| VERSILON DUALITY | 100.87% | 766.57 | 102.33 | D43 | | opaque |
| HDPE | 99.2% | | | D65 | | opaque |
| TYGON SE-200 | 98.06% | 125.32 | 25.22 | A67 | 2000 | clear |
| VERSILON PTFE | 96.01% | | | D58 | | clear |
| LLDPE | 90.96% | | | D44 | | opaque |
| VITON VITUBE | 88.80% | 59.15 | 13.31 | A60-75 | 1450 | opaque |
| TYGON 2475 HI PURITY | 86.27% | 213.91 | 29.76 | A72 | 2000 | clear |
| TYGON 2001 | 76.30% | 132.16 | 24.24 | A69 | 800 | clear |
| TYGON 2375 | 74.28% | | | A75 | 1900 | clear |
| EXCELON RNT | 59.55% | | | A68 | | clear |
| SILICONE 1/4" | 26.36% | | | A50 | 1100 | opaque |

As will be apparent, many of the tubing materials that are available that provide the highest recovery of hypochlorite active agent were relatively inflexible, or very difficult to compress, making them unsuitable for use in a peristaltic pump application. At this stage, the VITON, TYGON 2001, AND TYGON SE-200 seemed appropriate based on flexibility values and hypochlorite recovery.

While the VITON tubing showed hypochlorite recovery of over 88% after a 24 hour soak, this recovery value dropped to about 75% after a 2 week soak. TYGON 2001 tubing showed a hypochlorite recovery of 76.3% after a 24 hour soak. Based on these initial data, VITON tubing was tested within the spraying system with a peristaltic pump, and several problems were noted. Pressure build up occurred in the tubing, even after spraying was finished, causing the composition to continue to "spurt" out, after spraying had finished, as mentioned above. Perhaps most importantly, the VITON tubing material ripped apart within 72 hours of test use within the peristaltic pump, which was likely due to friction between the rollers and the tubing. In addition because the VITON tubing is opaque, the user could not see the liquid flow within the tubing.

Because of the difficulties with the VITON tubing material, the TYGON 2001 material was tested, and found to be suitable for use. It exhibits hypochlorite recovery of 76.3% after 24 hours of contact, it is clear (which advantageously allows the user to view flow of the composition through tubing 108), it includes a stiffness value that is between from 120 $lb_f$/in and 135 $lb_f$/in, and it includes a force to closure value that is between from 20 $lb_f$ and 30 $lb_f$. Such characteristics have been found by the present inventors to provide sufficient durability and robustness, while also being sufficiently flexible for use with a peristaltic pump. This tubing material exhibited acceptable compatibility with hypochlorite bleach, as well as high compatibility with an alternative quaternary amine disinfecting agent. For example, in at least some embodiments, the present spraying systems and methods allow for use of either a hypohalite-based disinfecting composition, or a quaternary amine-based disinfecting composition. The tubing materials and other parameters identified herein allow use of either or both such compositions, interchangeably, allowing the system and method to be compatible and easily usable with either such disinfecting composition.

An example of such an alternative quaternary-amine based disinfecting composition is available from STEPAN under the EPA registration 1839-220. By way of example, such a composition includes as active ingredients, a mixture of alkyl dimethyl benzyl ammonium chlorides and a mixture of alkyl dimethyl ethylbenzyl ammonium chlorides. For example, the particular formulation associated with EPA registration 1839-220 includes 0.15% of each of the above classes of quaternary ammonium compounds. The mixture of alkyl dimethyl benzyl ammonium chlorides includes alkyl chain lengths of 60% $C_{14}$, 30% $C_{16}$, 5% $C_{12}$, and 5% $C_{18}$. The mixture of alkyl benzyl ammonium chlorides includes alkyl chain lengths of 68% $C_{12}$ and 32% $C_{14}$. It will be apparent that other quaternary amine compounds, mixtures of various quaternary amines, or other disinfecting agents may alternatively or additionally be used. While the above example includes 0.3% quaternary amines, it will be apparent that the range of quaternary amine disinfecting agent may vary, e.g., from about 0.01% to about 2%, or from 0.05% to about 1%, or from 0.1% to about 0.5% by weight.

Returning to the description of tubing materials, the present inventors discovered that tubing materials cannot be easily selected for applications including a peristaltic pump, particularly for uses in which contact with hypochlorite or other hypohalite bleach disinfecting agents will occur. Tubing properties provided in manufacturer specification sheets, such as durometer hardness, tensile strength, and compression set do not provide sufficient information to determine if a tubing material will be suitable for use in a peristaltic pump application, not to mention whether such tubing material will exhibit sufficient compatibility with a quaternary amine or hypohalite disinfecting agent. The specific properties measured and recorded above (e.g., such as stiffness and force to orifice closure) far are more relevant to indicating whether the material will be suitable for use in an application including a peristaltic pump. In addition, as the inventors found, most types of tubing which have minimal interaction with hypohalite disinfecting agents (e.g., HDPE, LDPE, PET) are far too stiff and inflexible for use in such applications.

The inventors discovered something of a "sweet spot" with respect to stiffness and force to closure is needed in order to provide sufficient durability and robustness for use in peristaltic pump uses, while also providing sufficient flexibility to allow the tubing material to be bent, flexed, and manipulated as needed by the user during operation (not to mention the ability to wrap around a peristaltic pump at a relatively tight curvature, as seen in FIG. 2). As noted above, values of stiffness that are from 120 $lb_f/in$ to 135 $lb_f/in$, (e.g., from 122 $lb_f/in$ to 133 $lb_f/in$) and force to closure values that are from 20 $lb_f$ to 30 $lb_f$ (e.g., from 22 $lb_f$ to 26 $lb_f$) advantageously allow the tubing material to balance the needed characteristics. Exemplary materials listed in Table 1 including such characteristics, while also providing a hypochlorite recovery of at least 65% (a loss of no more than 35%) include at least TYGON SE-200 and TYGON 2001. The stiffness and force to closure values of some of the materials listed in Table 1 were not yet tested (e.g., TYGON 2375), but may prove suitable for use, so long as they exhibit stiffness and/or force to closure values as noted above. In addition, it will be appreciated that various other tubing materials may also meet the identified requirements.

Both TYGON SE-200 and TYGON 2001 are proprietary, clear PVC materials, which may be specially formulated to reduce or eliminate the inclusion of plasticizer materials within the tubing material. Other TYGON tubing materials (e.g., TYGON 2375) are also believed to be formed from PVC, without incompatible plasticizers. It is believed that plasticizers routinely added to such PVC tubing materials (e.g., such as in the EXCELON RNT tubing) are incompatible with the hypochlorite or other hypohalite active agent included in a hypohalite-based disinfecting composition. TYGON SE-200 is believed to include a fluorinated ethylene propylene liner or layer over the base PVC material.

TYGON 2001 is described as being plasticizer and oil free, and meets the FDA criteria for food contact. Other suitable TYGON tubing materials may also exhibit similar characteristics. TYGON 2001, TYGON SE-200, and TYGON 2375 have the following physical characteristics, as shown below in Table 2. While at least TYGON 2001 and TYGON SE-200 are suitable materials for use within the presently described spraying systems and methods, where a peristaltic pump is employed, it will be appreciated that other tubing materials meeting the above described key characteristics relative to stiffness, compression force to orifice closure, and hypochlorite recovery may also be suitable for use.

TABLE 2

| Property | ASTM Method | TYGON 2001 | TYGON SE-200 | TYGON 2375 |
|---|---|---|---|---|
| Durometer Shore A | D2240-03 | 69 | — | 75 |
| Color | — | Clear | Clear | Clear |
| Tensile Strength (psi) | D412-98 | 800 | 2000 | 1900 |
| Ultimate Elongation, % | D412-98 | 500 | 350 | 850 |
| Tear Resistance ($lb_f$/M) | D1004-03 | 140 | 165 | 240 |
| Specific Gravity | D792-00 | 0.88 | 1.45 | 0.9 |
| Water Absorption (24 hrs @ 23° C.) | D570-98 | 0.04 | <10.01 | <0.01 |
| Compression Set Constant Deflection, % @ 70° C. for 22 his | D395-03 Method B | 40 | 53 | 100 |
| Brittleness by Impact Temp (° C.) | D746-98 | −78 | −40 | <−75 |
| Maximum Recommended Operating Temp. (° C.) | — | 57 | 77 | 54 |
| Low Temp. Flexiblilty (° C.) | D380.94 | −73 | — | −75 |
| Dielectric Strength (V/mil) | D149-97 | 530 | 620 | — |
| Tensile Modulus @ 100% Elongation, psi | D412-98 | 240 | 650 | 425 |
| Tensile Set, % | D412-98 | 110 | 76 | 300 |

* Unless otherwise dictated, all tests were conducted at room temperature (73° F). Values shown were determined on 0.075" thick extruded strip or 0.075" thick molded ASTM plaques or molded ASTM durometer buttons.

While the disinfecting compositions may be based on a salt of hypochlorite (e.g., sodium hypochlorite) as the disinfecting agent, it will be appreciated that other disinfecting agents can alternatively or additionally be used. Non-limiting examples of such include other hypohalites (e.g., hypobromides, or other halides), other chlorine generating compounds (e.g., isocyanates and the like), hypohalous acids (e.g., hypochlorous acid), halogens, peroxides (e.g., hydrogen peroxide), and/or quaternary amines, and the like. Examples of hypochlorites include, but are not limited to alkali metal hypochlorites (e.g., sodium hypochlorite, potassium hypochlorite, and the like, alkali earth metal hypochlorites (e.g., calcium hypochlorite, magnesium hypochlorite, and the like). Combinations of hypochlorites may of course be employed.

The composition may have a viscosity so that it may readily be dispensed through a spraying system as described herein. For example, the compositions may have a viscosity of less than 10,000 cps, less than 1,000 cps, less than 100 cps, or less than 10 cps. In an embodiment, the viscosity may be approximately equal to that of water (e.g., 1 cps).

In an embodiment, particularly where the disinfecting composition contains a hypochlorite active agent, the pH may be less than 8, or less than 7. Even though hypochlorite active agents typically exhibit increased stability at elevated pH values (e.g., greater than 8, such as 9 to 13, or 9 to 12), in at least some embodiments, the disinfecting composition including a hypohalite active agent is specifically formulated to have a pH that is less than 8, or no more than 7, while still exhibiting good stability, and exhibiting higher microefficacy against bacteria, viruses or other microbes on a target surface being sprayed. For example, while hypohalites (e.g., sodium hypochlorite) may typically exhibit higher stability at relatively higher pH values, the microefficacy may be improved at somewhat lower pH values. The pKa value for sodium hypochlorite bleach solution is at about a pH of 7.4, meaning that this is the most unstable pH for such dilute hypochlorite solutions. As such, the disinfecting composition may have a pH of no more than 7, less than 7, no more than 6.7, from 5 to 7, from 5.5 to 7, from 5.5 to 6.7, from 6 to 7, from 6 to 6.7, or from 6 to 6.5.

Figure 4:
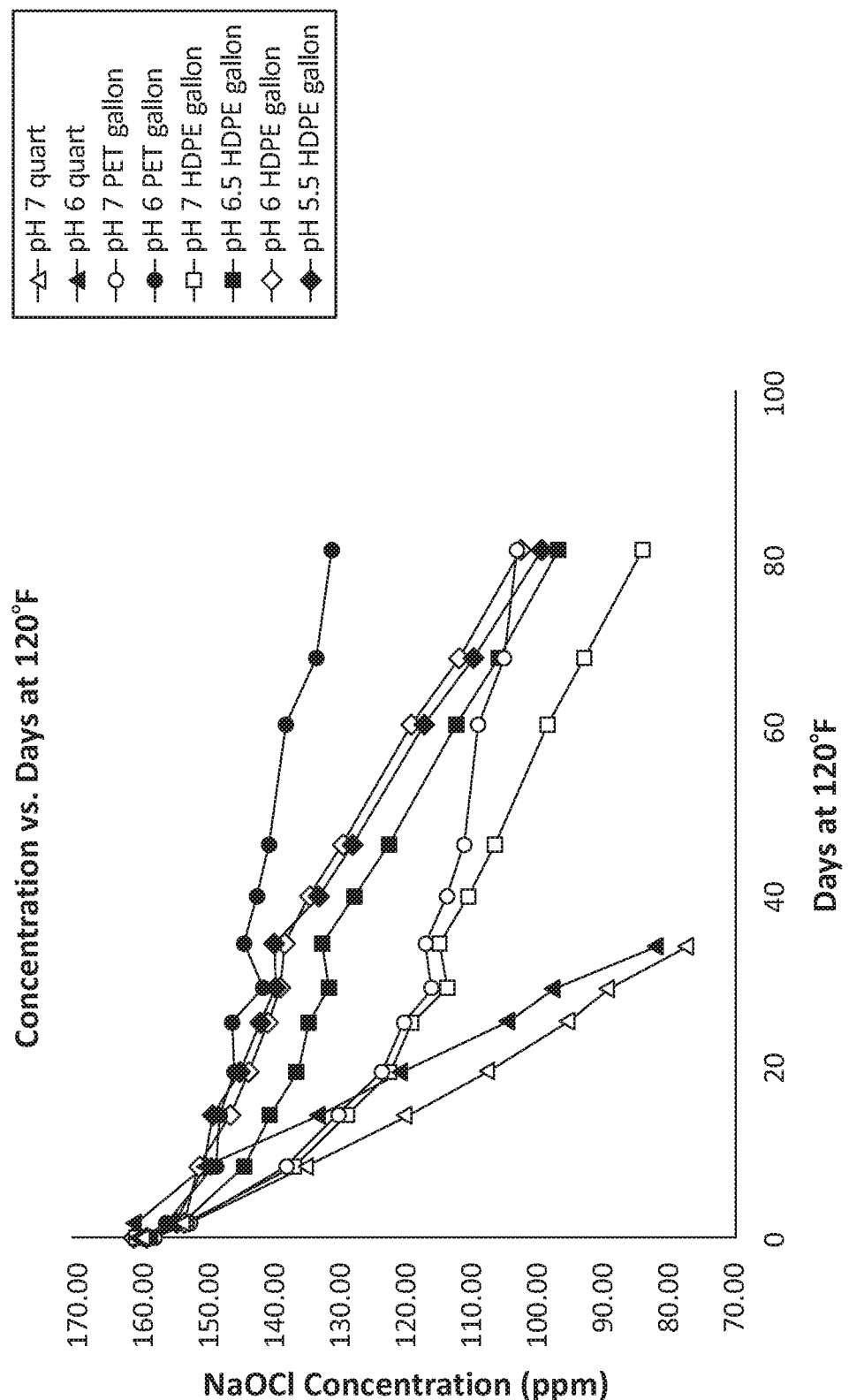
FIG. 4 shows sodium hypochlorite concentration for exemplary dilute sanitizing or disinfecting compositions over 80 days, at an elevated temperature of 120° F. 25 days at 120° F. approximately correlates to 1 year storage at ambient temperature (e.g., 70° F.).

FIG. 4 illustrates the effect of pH on hypohalite stability over time, at an elevated temperature of 120° F. FIG. 4 also shows the effect of the container material (e.g., HDPE or PET) on hypohalite stability. As shown in FIG. 4, by ensuring that the composition has a lower pH (e.g., pH of 6 to 6.7, or 6 to 6.5), loss of hypochlorite within the container (e.g., during storage, over the expected shelf-life of the composition) can be minimized or reduced to an acceptable degree. By way of example, a shelf life of the composition may be determined by the time it takes for the hypohalite concentration to drop to 120 ppm. 25 days at an elevated temperature of 120° F. may be approximately equivalent to 1 year of shelf-life at 70° F. As will be apparent from FIG. 4, using an appropriate container material and maintaining the dilute disinfecting composition at a pH of no more than 7 (e.g., no more than 6.7, or no more than 6.5) can achieve an expected 1 year or better shelf-life. A configuration as represented in FIG. 4, including an initial hypochlorite concentration of 160 to 165 ppm, and a pH of 6.7 or less is sufficient to ensure surface sanitization (e.g., at least 85 ppm hypochlorite as deposited on the target surface) even after 1 year of storage of the composition, under typical storage conditions.

The disinfecting composition may be dilute, such that it exhibits only a relatively low level of hypohalite concentration. For example, the concentration of hypohalite in the composition may be not greater than 500 ppm, not greater than 400 ppm, not greater than 300 ppm, not greater than 210 ppm, or not greater than 175 ppm. The concentration of hypohalite may be at least 85 ppm, at least 100 ppm, at least 120 ppm, or at least 150 ppm, e.g., from 150 ppm to 175 ppm, or 120 ppm to 210 ppm. While such dilute concentrations may be particularly suitable, it will be appreciated that higher concentrations may be suitable for use in at least some circumstances (e.g., up to 1,000 ppm, up to 2,000 ppm, or even up to 5,000 ppm).

For ease of use, the disinfecting composition may be provided at such a dilute hypohalite concentration, so that the user and/or spraying system does not need to further dilute the composition. Of course, it is within the scope of the present disclosure to provide a more concentrated composition, which may be diluted by the user and/or diluted by the spraying system (e.g., automatically, by mixing the concentrate with water) before spraying.

Upon spraying the disinfecting composition (e.g., as seen in FIG. 1), the concentration of hypohalite within the composition as sprayed onto the target surface may be at least 85 ppm, in order to provide the desired level of surface sanitization or disinfection. For example, even where the concentration of hypochlorite in the composition as it exits the spray nozzle is greater than 85 ppm (e.g., from 120 to 210 ppm), some fraction (e.g., as much as 20%) of the hypochlorite or other active agent may actually volatilize, and be lost, rather than reaching the surface 112 being treated. As will be apparent from the present description, some fraction of the hypochlorite may also be lost through contact with the tubing 108, or through other undesirable interactions. Thus, in at least some embodiments, the composition as provided to the user (e.g., in reservoir 102) may have a hypochlorite or other hypohalite concentration of 150 to 175 ppm, ensuring that the concentration actually reaching the target surface being sprayed is at least 85 ppm, even after 1 year of storage of the disinfecting composition (e.g., at which point the hypohalite concentration therein may have dropped to as low as 120 ppm). Even where some losses may occur within the spraying system itself (e.g., within tubing 108), and some hypohalite may be lost to volatilization upon exiting nozzle 104, such losses can be accounted for and acceptably accommodated, to still ensure an efficacious deposition of at least 85 ppm hypohalite.

The system, method, and composition may be configured to provide dispensed disinfection composition having particular particle size, and under particular air flow characteristics. For example, flow may be from 75 mL/min to 200 mL/min, 100 mL/min to 150 mL/min, or from 120 mL/min to 130 mL/min. Air pressure may be from 15 psi to 100 psi, from 25 to 50 psi, or from 30 psi to 40 psi. Air flow may be from 1 standard cubic feet per minute (SCFM) to 10 SCFM, from 2.5 SCFM to 5 SCFM, or from 3 SCFM to 4 SCFM. The parameters may be particularly selected to provide an average particle size for dispensed droplets having a size greater than 50 μm, greater than 60 μm, or greater than 65, e.g., from 50 μm to 150 μm, from 60 μm to 100 μm, or from 65 μm to 80 μm.

While principally described in the context of a disinfecting composition including a hypohalite (e.g., sodium hypochlorite) disinfecting agent, it will be appreciated that the present systems and methods are also suitable for use with disinfecting compositions that include a quaternary ammonium disinfecting agent. The present systems and methods thus allow a user to use either of such disinfecting compositions, interchanging between the two, and using whichever is desired, at any particular time or use.

The disinfecting compositions may include one or more surfactants, solvents, organic or mineral acids, chelating agents, fragrances, dyes, preservatives, humectants, polymers, pH adjusters, buffers, solubilizers, or other adjuvants employed in disinfecting compositions.

Examples of surfactants include, but are not limited to sulfates, sulfonates, betaines, alkyl polysaccharides, (e.g., alkyl polyglycosides, also known as alkyl polyglucosides), amine oxides, tweens, alcohol ethoxylates, and combinations thereof. The surfactant concentration may be any desired concentration. Examples may include up to 80%, up to 50%, up to 30%, up to 20%, or less than 10%, less than 5%, less than 4%, less than 3%, or less than 2% by weight, depending on the characteristics desired.

The surfactant(s) may include nonionic, anionic, cationic, ampholytic, amphoteric, zwitterionic surfactants, and mixtures thereof. A typical listing of anionic, ampholytic, and zwitterionic classes, and species of these surfactants, is given in U.S. Pat. No. 3,929,678 to Laughlin. A list of cationic surfactants is given in U.S. Pat. No. 4,259,217 to Murphy. Various alkyl polysaccharide surfactants are disclosed in U.S. Pat. No. 5,776,872 to Giret et al.; U.S. Pat. No. 5,883,059 to Furman et al.; U.S. Pat. No. 5,883,062 to Addison et al.; and U.S. Pat. No. 5,906,973 to Ouzounis et al. U.S. Pat. No. 4,565,647 to Llenado. Various nonionic surfactants can be found in U.S. Pat. No. 3,929,678 to Laughlin. Each of the above patents is incorporated by reference.

An organic acid (e.g., citric acid), or relatively weaker mineral acid (e.g., phosphoric acid) may be included, e.g., for pH adjustment, for cleaning, or the like. Where included, such an acid may be included in an amount of less than 5%, less than 4%, less than 3%, less than 2%, less than 1%, less than 0.5%, (e.g., from 0.01% to 2%, or from greater than 0.1% to about 1.5%).

Exemplary organic acid may include 2-hydroxycarboxylic acids or mixtures of two or more acids. Examples of such acids include, but are not limited to, tartaric acid, citric acid, malic acid, mandelic acid, oxalic acid, glycolic acid, lactic acid, and acetic acid.

If it were desired to adjust pH upward, a basic pH adjuster (e.g., sodium hydroxide, or another hydroxide), could be used, e.g., in any of the amounts described above relative to pH adjusting acids.

Solubilizers (e.g., to solubilize a fragrance or other oil), if present, could be included in an amount of less than 1%, less than 0.5%, less than 0.3% (e.g., from about 0.01% to 0.5%).

Dyes, fragrances, and/or preservatives, if present, may be included in an amount of less than 1%, or less than 0.5%.

The compositions, methods, and systems may be particularly well suited for use in public or commercial environments, such as airports, ambulances, gyms and other athletic facilities, bathrooms, correctional facilities, cruise ships, daycare centers, health clubs, hotels, institutional kitchens, laundry rooms, offices, restaurants, and schools, to name just a few. Of course, use in the home or other locations may also be appropriate.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

The invention claimed is:

1. A dilute hypohalite sanitizing or disinfecting composition for use in a spraying system for dispensing the dilute hypohalite sanitizing or disinfecting composition through the spraying system, wherein the spraying system includes a hand-held spray nozzle through which the aqueous hypohalite sanitizing or disinfecting composition is sprayed during use, and a pump and associated tubing for conveying the aqueous hypohalite sanitizing or disinfecting composition from a reservoir to the hand-held spray nozzle, the dilute hypohalite sanitizing or disinfecting composition comprising:
   (a) water; and
   (b) a hypohalite at a concentration from 150 ppm to 200 ppm;
   (c) wherein the hypohalite composition has a pH of no more than 8;
   (d) wherein the dilute hypohalite composition exhibits at least a 65% recovery of hypohalite after 24 hours of contact between the hypohalite composition and the associated tubing of the spraying system and wherein the associated tubing comprises one or more of TYGON SE-200 or TYGON 2001;
   (e) wherein the aqueous hypohalite sanitizing or disinfecting composition maintains a concentration of hypohalite of about 85 ppm to 200 ppm as sprayed onto a target surface to be sanitized or disinfected.

2. The composition of claim 1, wherein the hypohalite sanitizing or disinfecting composition has a pH from 5.5 to not more than 8.

3. The composition of claim 1, wherein the hypohalite sanitizing or disinfecting composition has a pH from 5.5 to 6.7.

4. The composition of claim 1, wherein the aqueous hypohalite sanitizing or disinfecting composition has a concentration of hypohalite that is between 150 ppm and 175 ppm.

5. A dilute hypohalite sanitizing or disinfecting composition for use in a spraying system for dispensing the dilute hypohalite sanitizing or disinfecting composition through the spraying system, wherein the spraying system includes a hand-held spray nozzle through which the aqueous hypohalite sanitizing or disinfecting composition is sprayed during use, and a pump and associated tubing for conveying the aqueous hypohalite sanitizing or disinfecting composition from a reservoir to the hand-held spray nozzle, the dilute hypohalite sanitizing or disinfecting composition comprising:
   (a) water; and
   (b) a hypohalite at a concentration from 150 ppm and 200 ppm;
   (c) wherein the hypohalite composition has a pH of no more than 8;
   (d) wherein the dilute hypohalite composition exhibits at least a 65% recovery of hypohalite after 24 hours of contact between the hypohalite composition and the associated tubing of the spraying system wherein the associated tubing has a stiffness from 120 $lb_f$/in to 135 $lb_f$/in and a compression force to closure of from 20 $lb_f$ to 30 $lb_f$;
   (e) wherein the aqueous hypohalite sanitizing or disinfecting composition maintains a concentration of hypohalite of about 85 ppm to 200 ppm as sprayed onto a target surface to be sanitized or disinfected.

* * * * *